(12) United States Patent
Gómez Bahamonde et al.

(10) Patent No.: US 12,251,376 B2
(45) Date of Patent: Mar. 18, 2025

(54) COMBINATIONS WITH THIAZOLIDINEDIONES FOR USE IN THE PREVENTION OR TREATMENT OF ABNORMAL BONE GROWTH

(71) Applicants: SERVIZO GALEGO DE SAÚDE (SERGAS), Santiago de Compostela, A Coruña (ES); FUNDACIÓN PÚBLICA GALEGA INSTITUTO DE INVESTIGACIÓN SANITARIA DE SANTIAGO DE COMPOSTELA, Santiago de Compostela (ES)

(72) Inventors: Rodolfo Gómez Bahamonde, Santiago de Compostela (ES); Eloi Franco Trepat, Santiago de Compostela (ES); Ana Alonso Pérez, Santiago de Compostela (ES); María Guillán Fresco, Santiago de Compostela (ES); Alberto Jorge Mora, Santiago de Compostela (ES)

(73) Assignees: SERVIZO GALEGO DE SAÚDE (SERGAS), Santiago de Compostela (ES); FUNDACIÓN PÚBLICA GALEGA INSTITUTO DE INVESTIGACIÓN SANITARIA DE SANTIAGO DE COMPOSTELA, Santiago de Compostela (ES)

( * ) Notice: Subject to any disclaimer, the term of this patent is extended or adjusted under 35 U.S.C. 154(b) by 601 days.

(21) Appl. No.: 17/429,902

(22) PCT Filed: Feb. 10, 2020

(86) PCT No.: PCT/EP2020/053344
§ 371 (c)(1),
(2) Date: Aug. 10, 2021

(87) PCT Pub. No.: WO2020/165101
PCT Pub. Date: Aug. 20, 2020

(65) Prior Publication Data
US 2022/0288044 A1     Sep. 15, 2022

(30) Foreign Application Priority Data
Feb. 11, 2019 (EP) .................... 19382094

(51) Int. Cl.
| A61K 31/405 | (2006.01) |
| A61K 31/4439 | (2006.01) |
| A61K 31/573 | (2006.01) |
| A61P 19/08 | (2006.01) |

(52) U.S. Cl.
CPC ........ *A61K 31/4439* (2013.01); *A61K 31/405* (2013.01); *A61K 31/573* (2013.01); *A61P 19/08* (2018.01)

(58) Field of Classification Search
CPC .............. A61K 31/4439; A61K 31/405; A61K 31/573; A61P 19/08
USPC ......................................................... 514/171
See application file for complete search history.

(56) References Cited

FOREIGN PATENT DOCUMENTS

| CN | 106754664 A | 5/2017 |
| CN | 108057031 A | 5/2018 |
| CN | 108192860 A | 6/2018 |
| WO | 2010037130 A2 | 4/2010 |
| WO | 2010037130 A3 | 5/2010 |
| WO | 2013006372 A1 | 1/2013 |

OTHER PUBLICATIONS

Contador D, Ezquer F, Espinosa M, Arango-Rodriguez M, Puebla C, Sobrevia L, Conget P. Dexamethasone and rosiglitazone are sufficient and necessary for producing functional adipocytes from mesenchymal stem cells. Exp Biol Med (Maywood). Sep. 2015; 240(9):1235-46. (Year: 2015).*
Jiao Li, Bin Zuo, Li Zhang, Liming Dai, Xiaoling Zhang; Osteoblast versus Adipocyte: Bone Marrow Microenvironment-Guided Epigenetic Control. Case Rep Orthop Res Jan. 11, 2019; 1 (1-3): 2-18. Published online Jun. 7, 2018 (Year: 2018).*
Sinha S, Uchibe K, Usami Y, Pacifici M, Iwamoto M. Effectiveness and mode of action of a combination therapy for heterotopic ossification with a retinoid agonist and an anti-inflammatory agent. Bone. Sep. 2016;90:59-68. (Year: 2016).*
Takahashi et al., "Induction of Pluripotent Stem Cells from Mouse Embryonic and Adult Fibroblast Cultures by Defined Factors," *Cell* 126:663-676, Aug. 25, 2006. (14 pages).
Waddington, "The Strategy of the Genes: A Discussion of Some Aspects of Theoretical Biology," *Routledge Library Editions: 20th Century Science 20*, 2014. (275 pages).
Anghel et al., "Fat poetry: a kingdom for PPARγ," *Cell Research* 17:486-511, Jun. 12, 2007. (26 pages).
Gatti et al., "Rosiglitazone Therapy is Associated with Major Clinical Improvements in a Patient With Fibrodysplasia Ossificans Progressiva," *Journal of Bone and Mineral Research* 25(6):1460-1462, Jun. 2010 [Published online Nov. 23, 2009]. (3 pages).
Hegele, "Lessons from human mutations in PPARγ," *International Journal of Obesity* 29:S31-S35, Apr. 2005. (6 pages).
Janderová et al., "Human Mesenchymal Stem Cells as an in Vitro Model for Human Adipogenesis," *Obesity Research* 11(1):65-74, Jan. 2003. (10 pages).

(Continued)

*Primary Examiner* — Yevgeny Valenrod
(74) *Attorney, Agent, or Firm* — Seed IP Law Group LLP

(57) ABSTRACT

The present invention refers to the use of thiazolidinediones (preferably rosiglitazone and/or pioglitazone) in the prevention or treatment abnormal bone growth selected from the list comprising: heterotopic ossification, osteophytes and/or syndesmophytes. According to the present invention, thiazolidinediones can be combined with corticoids and/or anti-inflammatory drugs (preferably non-steroidal anti-inflammatory drugs).

10 Claims, 10 Drawing Sheets

(56) References Cited

OTHER PUBLICATIONS

Lowell, "PPARγ: An Essential Regulator of Adipogenesis and Modulator of Fat Cell Function," *Cell* 99:239-242, Oct. 29, 1999. (4 pages).
Sandhu et al., "LDL-cholesterol concentrations: a genome-wide association study," *Lancet* 371:483-491, Feb. 9, 2008. (9 pages).
Shockley et al., "PPARγ2 Regulates a Molecular Signature of Marrow Mesenchymal Stem Cells," *PPAR Research* 2007:81219, Aug. 23, 2007. (13 pages).
Yun et al., "Inhibition of PPARγ2 Gene Expression by the HIF-1-Regulated Gene DEC1/Stra13: A Mechanism for Regulation of Adipogenesis by Hypoxia," *Developmental Cell* 2:331-341, Mar. 2002. (11 pages).

\* cited by examiner

A

B

C

D

A

B

A

B

C

D

A

B

A

B

A

B

C

COMBINATIONS WITH THIAZOLIDINEDIONES FOR USE IN THE PREVENTION OR TREATMENT OF ABNORMAL BONE GROWTH

FIELD OF THE INVENTION

The present invention also discloses that other compounds boost the effect of thiazolidinediones blocking osteoblast differentiation and promoting adipocyte differentiation. Among these compounds, the present invention specifically refers to corticoids such as dexamethasone, and NSAID (Nonsteroidal anti-inflammatory drugs like) indomethacin, which shows a clear synergistic effect in the prevention of heterotopic ossification.

STATE OF THE ART

Abnormal bone growth is a pathological condition that may occur in different situations. Particularly, this abnormal bone may be formed in soft tissues (heterotopic ossification) or also on the surface of a bone (osteophytes and/or syndesmophytes).

Osteophytes are bony projections that form along joint margins. Osteophytes form because of the increase in a damaged joint's surface area. This is most common from the onset of arthritis.

A syndesmophyte is a bony growth originated inside a ligament, commonly seen in the ligaments of the spine, specifically the ligaments in the intervertebral joints leading to fusion of vertebrae. Syndesmophytes are pathologically similar to osteophytes. They are commonly seen in patients who have had back surgery or other chronic stresses on the ligaments of their spine.

Heterotopic ossification is the process by which bone tissue forms outside of the skeleton, particularly in soft tissues. In other words, heterotopic ossification is the presence of bone in soft tissue where bone normally does not exist.

In traumatic heterotopic ossification, the patient may complain of a warm, tender, firm swelling in a muscle and decreased range of motion in the joint served by the muscle involved. There is often a history of a blow or other trauma to the area a few weeks to a few months earlier. Patients with traumatic neurological injuries, severe neurologic disorders or severe burns who develop heterotopic ossification experience limitation of motion in affected areas.

Heterotopic ossification can be caused by surgery or trauma to the hips and legs. About every third patient who has total hip arthroplasty (joint replacement) or a severe fracture of the long bones of the lower leg will develop heterotopic ossification but is uncommonly symptomatic. Between 50% and 90% of patients who developed heterotopic ossification following a previous hip arthroplasty will develop additional heterotopic ossification.

Heterotopic ossification often develops in patients with traumatic brain or spinal cord injuries, other severe neurologic disorders or severe burns, most commonly around the hips. The mechanism is unknown. This may account for the clinical impression that traumatic brain injuries cause accelerated fracture healing.

There are also rare genetic disorders causing heterotopic ossification such as fibrodysplasia ossificans progressiva (FOP), a condition that causes injured bodily tissues to be replaced by heterotopic bone. Characteristically exhibiting in the big toe at birth, it causes the formation of heterotopic bone throughout the body over the course of the sufferer's life, causing chronic pain and eventually leading to the immobilisation and fusion of most of the skeleton by abnormal growths of bone.

Another rare genetic disorder causing heterotopic ossification is progressive osseous heteroplasia (POH), is a condition characterized by cutaneous or subcutaneous ossification.

Regarding the diagnosis, during the early stage, an x-ray will not be helpful because there is no calcium in the matrix. Early laboratory tests are not very helpful. Alkaline phosphatase will be elevated at some point, but initially may be only slightly elevated, rising later to a high value for a short time. Unless weekly tests are done, this peak value may not be detected. It is not useful in patients who have had fractures or spine fusion recently, as they will cause elevations.

The only definitive diagnostic test in the early acute stage is a bone scan, which will show heterotopic ossification 7-10 days earlier than an x-ray. The three-phase bone scan may be the most sensitive method of detecting early heterotopic bone formation. However, an abnormality detected in the early phase may not progress to the formation of heterotopic bone. Another finding, often misinterpreted as early heterotopic bone formation, is an increased (early) uptake around the knees or the ankles in a patient with a very recent spinal cord injury. It is not clear exactly what this means, because these patients do not develop heterotopic bone formation. It has been hypothesized that this may be related to the autonomic nervous system and its control over circulation.

When the initial presentation is swelling and increased temperature in a leg, the differential diagnosis includes thrombophlebitis. It may be necessary to do both a bone scan and a venogram to differentiate between heterotopic ossification and thrombophlebitis, and it is even possible that both could be present simultaneously. In heterotopic ossification, the swelling tends to be more proximal and localized, with little or no foot/ankle edema, whereas in thrombophlebitis the swelling is usually more uniform throughout the leg.

With respect to the treatment, there is no clear form of treatment. Originally, bisphosphonates were expected to be of value after hip surgery but there has been no convincing evidence of benefit, despite having been used prophylactically. Depending on the growth's location, orientation and severity, surgical removal may be possible. Prophylactic radiation therapy for the prevention of heterotopic ossification has been employed since the 1970s. A variety of doses and techniques have been used. Generally, radiation therapy should be delivered as close as practical to the time of surgery. A dose of 7-8 Gray in a single fraction within 24-48 hours of surgery has been used successfully. Treatment volumes include the periarticular region, and can be used for hip, knee, elbow, shoulder, jaw or in patients after spinal cord trauma. Single dose radiation therapy is well tolerated and is cost effective, without an increase in bleeding, infection or wound healing disturbances. However, radiotherapy is not actually used in children. Moreover, although radiotherapy offers a clear improvement in the rate of recurrence and appearance of heterotopic ossification, it is generally considered an aggressive and non-specific treatment.

On the other hand, certain anti-inflammatory agents, such as indomethacin, ibuprofen and aspirin, have shown some effect in preventing recurrence of heterotopic ossification after total hip replacement. Conservative treatments such as passive range of motion exercises or other mobilization techniques provided by physical therapists or occupational therapists may also assist in the prevention.

Consequently, it can be said that the strategies which are being used today for the prevention of heterotopic ossification are only showing partial results and some of them are very aggressive for the patients. So, finding an effective and non-aggressive treatment aimed at preventing the formation of heterotic bone is a clear unmet medical need.

The present invention is thus focused on solving the above-cited problem and provides an effective and non-aggressive treatment for preventing heterotopic ossification.

DESCRIPTION OF THE INVENTION

Brief Description of the Invention

The present invention provides an effective and non-aggressive treatment for preventing heterotopic ossification. Particularly, the present invention refers to the use of thiazolidinediones (preferably rosiglitazone and/or pioglitazone) in the prevention of heterotopic ossification, preferably in soft tissues. According to the present invention, thiazolidinediones might be combined with corticoids and/or anti-inflammatory drugs (preferably non-steroidal anti-inflammatory drugs).

The scientific concept behind this invention is that osteoblastogenesis and adipogenesis are opposing mechanisms. This means that the stimuli that promote the differentiation of mesenchymal stem cells (MSCs) to osteoblasts inhibit their differentiation to adipocytes, and vice versa. Accordingly, it has been observed in the present invention that an adipogenic environment inhibit osteoblasts growth.

Specifically, the present invention shows that thiazolidinediones (rosiglitazone and pioglitazone) inhibit WNT pathway activation, which is essential for osteoblast differentiation and for the formation of new bone.

Additionally, thiazolidinediones also activate major intracellular pro-adipogenic pathways based on their agonist action over PPARG receptors. This explains their ability to inhibit osteoblast differentiation.

The present invention also discloses that other compounds boost the effect of thiazolidinediones blocking osteoblast differentiation and promoting adipocyte differentiation. Among these compounds, the present invention specifically refers to corticoids such as dexamethasone, and NSAID (Nonsteroidal anti-inflammatory drugs like) indomethacin, which shows a clear synergetic effect in the prevention of heterotopic ossification.

So, core idea of this invention is that thiazolidinediones, alone or in combination with corticoids and NSAID, prevent the differentiation of osteoblasts precursor cells to mature osteoblasts by inhibiting specific bone anabolic pathways and promoting certain pro-adipogenic pathways. This involves that thiazolidinediones and the combinations above mentioned could be useful for the treatment and prevention of the heterotopic bone formation.

So, the first embodiment of the present invention refers to thiazolidinediones for use in the prevention or treatment of abnormal bone growth selected from the list comprising: heterotopic ossification, osteophytes and/or syndesmophytes. In a preferred embodiment, the present invention refers to thiazolidinedione for use in the prevention or treatment of heterotopic ossification in soft tissues.

Consequently, the present invention is mainly directed to the treatment or prevention of heterotopic ossification, which can be defined as an abnormal bone growth in soft tissues. However, it is important to note that the compounds and compositions included in the present invention can be used, in a broad sense, for the treatment or prevention of abnormal bone growth, both in soft tissues (heterotopic ossification) or on the surface of a bone (for example osteophytes or syndesmophytes). Regarding osteophytes, the compounds and compositions of the present invention would be able to prevent their recurrence once they have been removed by surgery. The dosage and routes of administration would be the same used to treat or prevent heterotopic ossification.

Thiazolidinediones are a class of heterocyclic compounds consisting of a five-membered $C_3NS$ ring. Chemically, the members of this class are derivatives of the parent compound thiazolidinedione, and mainly include: Pioglitazone, rosiglitazone or lobeglitazone. The only approved use of the thiazolidinediones is in diabetes mellitus type 2. In a preferred embodiment of the invention, the thiazolidinediones are used in the present invention in combination with corticoids and/or anti-inflammatory drugs (preferably non-steroidal anti-inflammatory drugs). In a preferred embodiment, the thiazolidinedione which is used in the present invention is rosiglitazone or pioglitazone, preferably pioglitazone. In a preferred embodiment, the corticoid used in the present invention is dexamethasone. In a preferred embodiment, the non-steroidal anti-inflammatory drug is a COX-inhibitor, preferably indomethacin. In a preferred embodiment of the invention, the thiazolidinedione, the corticoid and/or the anti-inflammatory drug are administered respectively in any order; before, after or simultaneously to the administration of any of the other two active principles. In a preferred embodiment of the invention, the thiazolidinedione, the corticoid and/or the anti-inflammatory drug are administered following a route selected from: oral administration, intravenous administration or local administration. In a preferred embodiment of the invention, the thiazolidinediones, preferably combined with corticoids and/or anti-inflammatory drugs (preferably non-steroidal anti-inflammatory drugs), are used in the acute or chronic prevention of heterotopic ossification, preferably in soft tissues.

Acute prevention or treatment would be recommended in those cases wherein heterotopic ossification is caused by traumatic injuries. Table 1 discloses some examples which could require an acute treatment of the patient:

TABLE 1

|  | Incidence |
| --- | --- |
| Spinal Cord Injury (SCI) | 50% (20% strong symptoms) |
| Arthroplasty | Up to 90% (wide range) |
| Burns | 0.1-20% (size dependent) |
| Muscle and tendon injuries | 9-14% muscle contusions |
| Severe extremity injury | 63% |
| SCI or traumatic brain injury (TBI) + fractures or dislocations | 89% |

On the other hand, chronic prevention or treatment would be recommended in those cases wherein heterotopic ossification is caused by a genetic predisposition such as: PHP (Pseudohipoparathyroidisim), PPHP (Pseudopseudohypoparathyroidism), POH (Progressive Osseous Heteroplasia) or FOP (Fibrodysplasia ossificans progressiva).

The second embodiment of the present invention refers to a combination drug product (hereinafter composition of the invention) comprising a thiazolidinedione, a corticoid and/or an anti-inflammatory drug (preferably a non-steroidal anti-inflammatory drug). In a preferred embodiment, the combination drug product comprises rosiglitazone or pioglitazone, dexamethasone and indomethacin. In a preferred embodiment, said combination drug product used in the prevention of the formation of heterotopic bone, preferably in soft tissues.

The third embodiment of the present invention refers to a pharmaceutical composition comprising the above-cited combination drug product of and optionally pharmaceutically acceptable carriers.

The fourth embodiment of the present invention refers a method for the prevention of abnormal bone growth which comprises administering to the patient a therapeutically effective amount of a composition comprising thiazolidinediones (rosiglitazone and/or pioglitazone) preferably combined with corticoids and/or anti-inflammatory drugs (preferably non-steroidal anti-inflammatory drugs).

The most preferred embodiment of the present invention refers to a combination drug product comprising a thiazolidinedione, a corticoid and a non-steroidal anti-inflammatory drug for use in the prevention or treatment of abnormal bone growth selected from the list comprising: heterotopic ossification, osteophytes and/or syndesmophytes. Alternatively, this most preferred embodiment refers to a method for the prevention or treatment of abnormal bone growth selected from the list comprising: heterotopic ossification, osteophytes and/or syndesmophytes, which comprises the administration to the patient of a therapeutically effective dose or amount the above cited combination drug product.

So, the present invention can be applied in several ways:

The use of thiazolidinediones alone or in combination with NSAID and corticoids could be useful to prevent trauma-associated heterotopic ossification. This use can be enhanced providing an injectable pharmaceutical presentation of pioglitazone (alone or in combination). Very often poly-traumatized patients, at higher risk of developing heterotopic ossification, are in coma and the pioglitazone cannot be orally administered to these patients.

The use of thiazolidinediones alone or in combination with NSAID and corticoids could be useful to prevent hip surgery-associated heterotopic ossification, which is a really frequent situation. Despite that we can treat the patients orally before the surgical procedure, providing an injectable pharmaceutical presentation of pioglitazone (alone or in combination) could allow the local administration of the treatment maximizing its activity. Additionally, the local administration of the therapy could strongly reduce the potential side effects of the treatment.

The use of thiazolidinediones alone or in combination with NSAID and corticoids could be useful to prevent the recurrence of heterotopic ossification associated to the excision surgery of an ectopic bone mass. Despite that we can treat the patients orally before the surgical procedure, providing an injectable pharmaceutical presentation of pioglitazone (alone or in combination) could allow the local administration of the treatment maximizing its function. Additionally, the local administration of the therapy could strongly reduce the potential side effects of the treatment.

The use of thiazolidinediones alone or in combination with NSAID and corticoids could be useful to prevent de novo, genetic or recurrent paediatric heterotopic ossification. Currently, for pioglitazone, there are not paediatric doses therefore new tablets formulations that allow an adequate paediatric dose adjustment will support this use in children. As described above an injectable formulation could allow the drug administration to coma patients as well as its local administration, which could improve its efficiency minimizing its side effects.

The use of thiazolidinediones alone or in combination with NSAID and corticoids could be useful to prevent and treat the ectopic bone formation linked the genetic variants of the heterotopic ossification, namely PHP, PPHP, POH or FOP. The preventive treatment of these patients should be chronic due to their genetic alterations promoting an excessive bone anabolism. Nonetheless a specific administration regimen could improve the management of these patients. Although we can treat the patients orally before a given surgical procedure or excision surgery, providing an injectable pharmaceutical presentation of pioglitazone (alone or in combination) could allow the local administration of the treatment maximizing its function. Additionally, the local administration of the therapy could strongly reduce the potential side effects of the treatment. Moreover, in these patients the local administration of the treatment would reduce the growth of an existing ectopic bone, which could prevent a subsequent excision surgery.

For the purpose of the present invention the following definitions are provided:

The term "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

"Therapeutically effective dose or amount" refers to that amount that achieves a positive prevention of heterotopic ossification in a subject. The degree of prevention will vary from subject to subject, depending on the species, age, and general condition of the subject, the severity of the condition being treated, mode of administration, and the like. An appropriate "effective" amount in any individual case may be determined by one of ordinary skill in the art using routine experimentation, based upon the information provided herein.

DETAILED DESCRIPTION OF THE INVENTION

Example 1. Material and Methods

Example 1.1. Reagents

Figure 1:
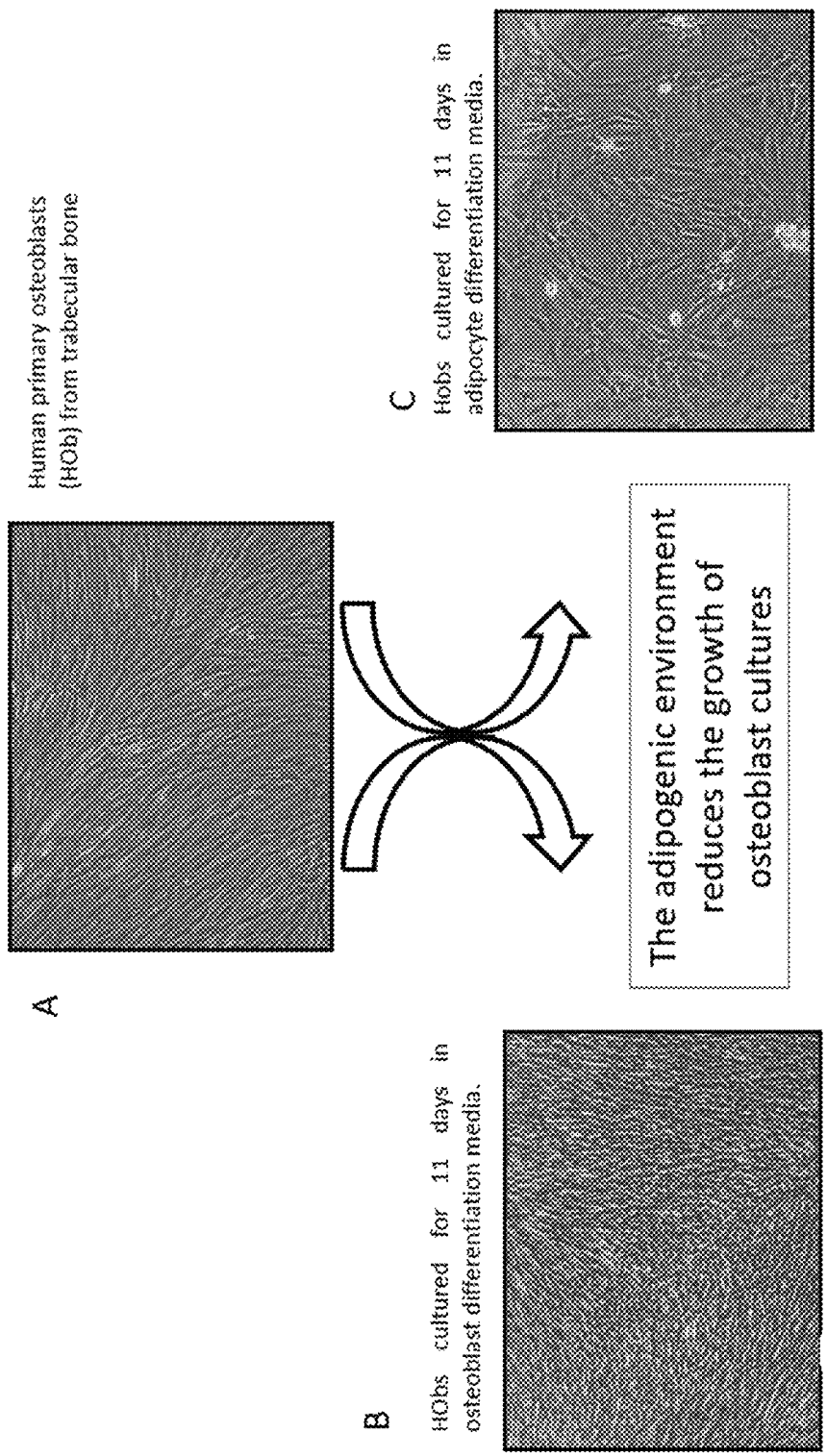
FIG. 1. Cell growth rate decreases with adipogenic media. This figure shows how the adipogenic media was able to dramatically reduce the proliferation rate of osteoblast cells. A) Human primary osteoblasts (HOb) from trabecular bone. B) HObs cultured for 11 days in osteoblast differentiation media. C) Hobs cultured for 11 days in adipocyte differentiation media.

All cell culture reagents were from Sigma (St. Louis, MO). For RT-PCR, a first strand kit was bought to (NZYtech, Portugal), the master mix was purchase to Thermo Fisher (Waltham, MA) and the primers were purchased from Sigma (St Louis, MO). EZNA Total RNA kit I isolation kits were from Omega Bio-Tek (Norcross, GA). LiCl, Rosiglitazone and Pioglitazone were from purchased from Sigma. Otherwise indicated all the products were purchased form Sigma (St. Louis, MO).

Example 1.2. Cell Cultures and Treatments

Adipogenic Environment Experiments in Primary Osteoblasts:

Human osteoblast-like cells were obtained from human bone explants. These bone fragments were set in a culture dish during 7 days in order to conditionate the media. After these days, medium was changed every two days. Along the first month, cells migrate from the bone to the dish. Once confluence is reached, bone fragments were withdrawn from the culture dish, and cells were used for experiments. For the evaluation of cell growth and morphology 45000 cells were seeded in P24 multi-well plates. After 24 hours, cells were treated with a cocktail for differentiation to osteoblasts, or a cocktail for differentiation to adipocytes for 11 days (changing medium every 2 days). After these days the photos revealing the growth of the cultures were taken using an inverted microscope (Leyca systems).

Adipocyte Differentiation Experiments:

Due to the elevated variability in the differentiation of human pre-adipocytes coming from different patients, murine cell line C3H10 was used for the adipocyte differentiation experiments, a well-known adipocyte differentiation model. To evaluate lipid droplets accumulation and for RT-PCR studies, 10000 cells were seeded in P24 multi-well plates until complete adhesion (6 h). Afterwards, the cells were treated during 7 days with a cocktail for adipocyte differentiation in presence or absence of rosiglitazone (2 µM) or pioglitazone (10 µM), dexamethasone (1 µM) and indomethacin (60 µM). After these days the photos revealing the intracellular accumulation of lipid droplets in the cell cultures were taken using an inverted microscope (Leyca systems).

Rosiglitazone and Pioglitazone were solubilized in DMSO. To avoid cytotoxicity, no more than 0.1% of DMSO was used as vehicle. All experiments were performed at least in triplicate.

WNT Pathway Experiments:

Due to the difficulty to obtain human pre-chondrogenic cell, to carry out the WNT pathway inhibition experiments, the murine chondrogenic cell line ATDC-5 was used. This cell line (purchased from RIKEN Cell Bank, Tsukuba, Japan) was cultured as suggested by the provider. This cell line mimics perfectly human chondrocyte metabolism.

For RT-PCR studies, 150.000 cells were seeded in P12 multi-well plates until complete adhesion (6 h) and then incubated overnight in serum-free conditions. Cells were treated with Rosiglitazone (2 µM) or Pioglitazone (10 µM) and later on co-treated with LiCl (20 mM) or Bio (1 µM) for 8 h. Rosiglitazone and Pioglitazone were solubilized in DMSO and LiCl and Bio in water. To avoid cytotoxicity, no more than 0.1% of DMSO was used as vehicle. All the experiments were performed at least in triplicate.

Osteoblast Differentiation Experiments:

Due to the elevated variability in the differentiation of human pre-osteoblasts coming from different patients, to carry out this study we used the human osteoblastic cell line SaOS2. This cell line (purchased from CLS Cell Bank) was cultured following manufacturer instructions. These cells have similar ALPL (alkaline phosphatase) activity, mineralization potential and gene regulation to primary osteoblasts.

For RT-PCR studies, 130000 cells were seeded in P6 multi-well plates until reaching confluence (1 week) changing the medium every 2 days. At that point, cells were treated with a cocktail for the differentiation to osteoblasts and treated with rosiglitazone (2 μM) or pioglitazone (10 μM), dexamethasone (1 μM), and indomethacin (60 μM) for 21 days (The medium was changed every 2 days).

Example 1.3. RNA Isolation and Real-Time Reverse Transcription—Polymerase Chain Reaction (RT-PCR)

RNA was extracted using an EZNA RNA isolation kit, according to the manufacturer's instructions. Murine AXIN2, FABP4, ADIPOQ, PLIN2, PPARG HPRT1 and human ALP, RUNX2, SPP1, BMP2, HPRT1 mRNA levels were determined using SYBR Green-based comparative PCR.

For relative quantification, it was performed an RT reaction with NZYtech First Strand Kit. Next, real-time PCR was performed with a Thermo Fisher Master Mix and specific primers for the above described genes. The reaction was performed in a Quant Studio 3 real time thermocycler from Thermo Fisher (Waltham, MA). Results of comparative real-time PCRs were analysed using QuantStudio Design & Analysis Software Thermo Fisher (Waltham, MA).

Example 1.4. Statistical Analysis

To determine the different gene expression the method used was the delta-CT method. Data are expressed as means±SEM of at least three independent experiments. Statistical analyses were performed by analysis of variance, followed by post hoc comparison testing (Student-Newman-Keuls test) in the GraphPad Prism 5 program; $p<0.05$ was considered significant.

Example 2. Results

Example 2.1. The Adipogenic Environment Reduces the Growth of Osteoblast Cultures In the present invention the fact that osteoblastogenesis and adipogenesis are opposite cell fates was validated by culturing primary human osteoblast cells (HObs) during 11 days in the presence of osteoblast differentiation media or adipocyte differentiation media. Such as it is shown in FIG. 1 adipogenic media was able to dramatically reduce the proliferation rate of these cells.

Figure 2:
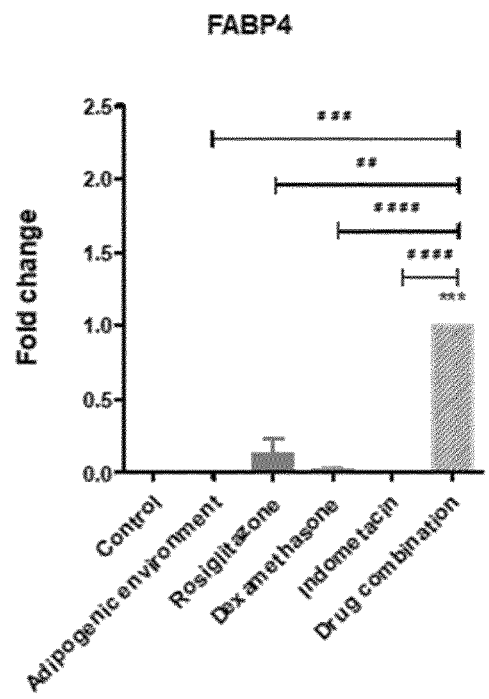
FIG. 2. Synergistic effect of the combination of rosiglitazone, dexamethasone and indomethacin on adipocyte differentiation. This figure shows the effect of the thiazolidinediones (rosiglitazone) on adipocyte differentiation and its synergistic effect with corticoids and NSAID. A precursor cell line was differentiated for 7 days to perform this experiment. It is observed that the effect of each of the drugs alone, or the adipogenic environment, is lower than the combination of the three drugs on the expression of key adipogenic marker genes A) FABP4, B) PLIN2, C) ADIPOQ and D) PPARG. * $p<0.05$; ** $p<0.01$; $p<0.001$ vs control. #$p<0.05$; ##$p<0.01$; ## #$p<0.001$ vs drug combination.
Figure 2:
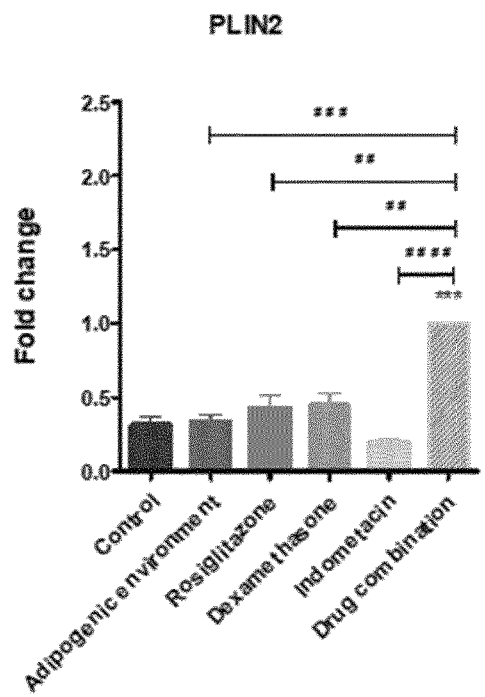
Figure 2:
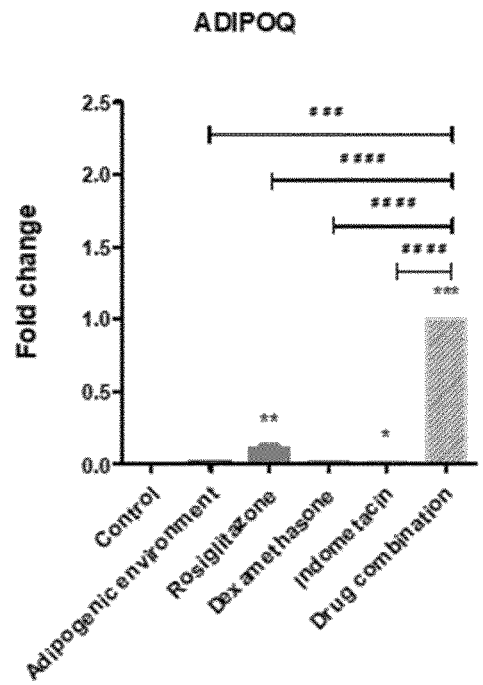
Figure 2:
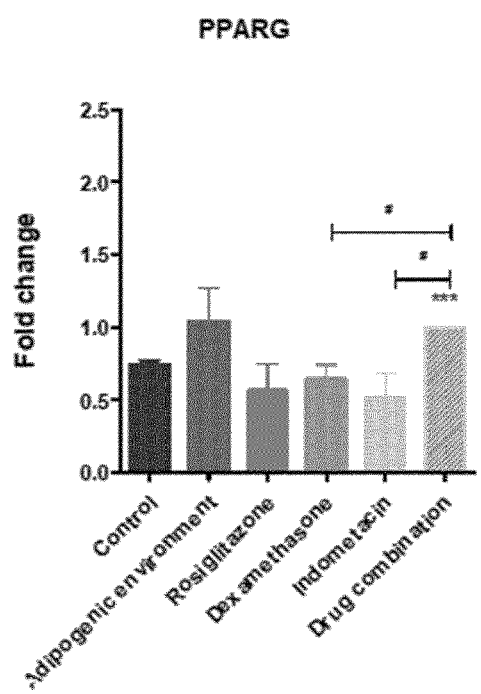
Figure 3:
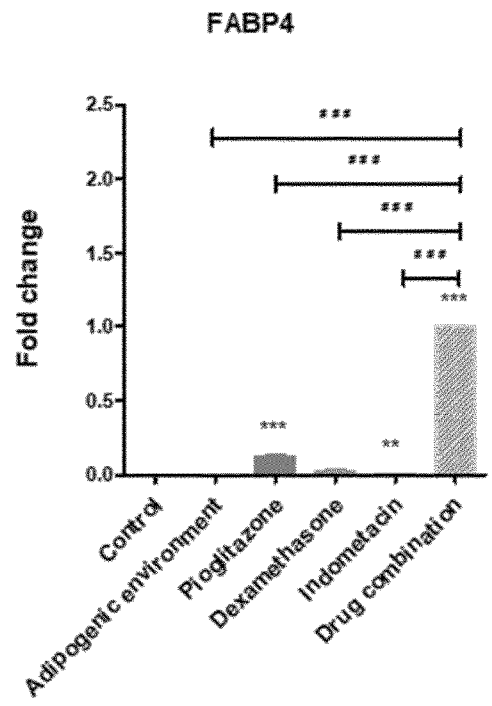
FIG. 3. Synergistic combination effect of the combination of pioglitazone, dexamethasone and indomethacin on adipocyte differentiation. This figure shows the effect of the thiazolidinediones (pioglitazone) on adipocyte differentiation and their synergistic effect with corticoids and NSAID. A precursor cell line was differentiated for 7 days to perform this experiment. It is observed that the effect of each of the drugs alone, or the adipogenic environment, is lower than the combination of the three drugs on the expression of key adipogenic marker genes: A) FABP4 and B) ADIPOQ). * $p<0.05$;  $p<0.01$; * $p<0.001$ vs control. #$p<0.05$; ##$p<0.01$; ## #$p<0.001$ vs drug combination.
Figure 3:
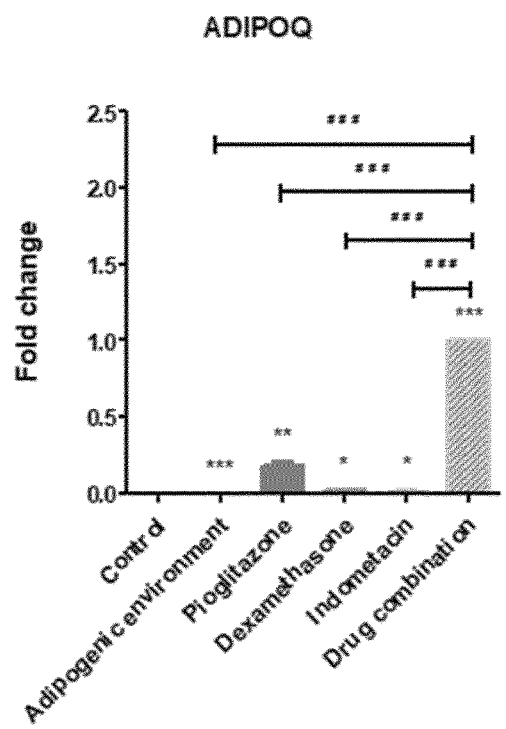
Figure 4:
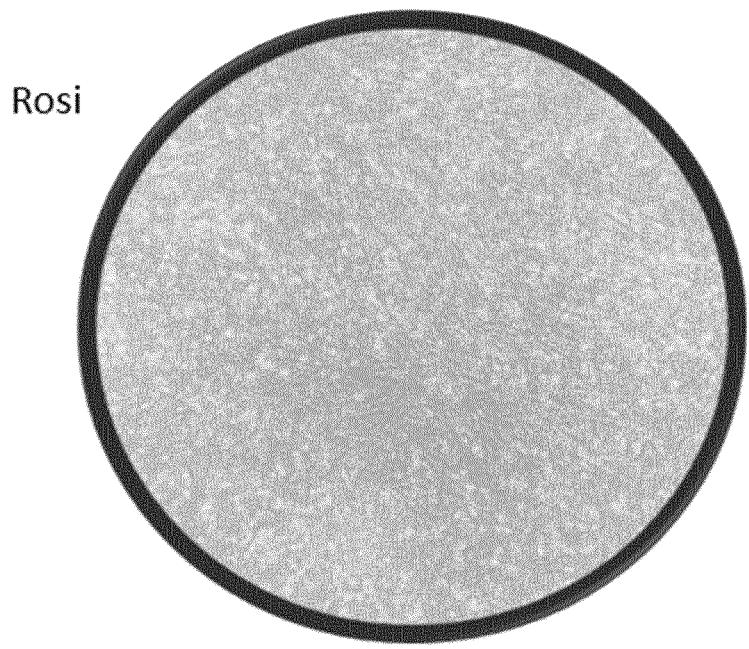
FIG. 4. Drug combination synergistically promotes the creation of lipid droplets. This figure shows the effect of the thiazolidinediones on adipocyte differentiation and their synergistic effect with corticoids and NSAID also in the early formation of lipid droplets in the cells. A) Rosi (rosiglitazone), B) Rosi (rosiglitazone)+Indo (indomethacin), C) Rosi (rosiglitazone)+DX (dexamethasone), and D) Rosi (rosiglitazone)+DX (dexamethasone)+Indo (indomethacin). The arrows show cells with an early accumulation of lipid droplets that are evidence of an ongoing adipogenesis.
Figure 4:
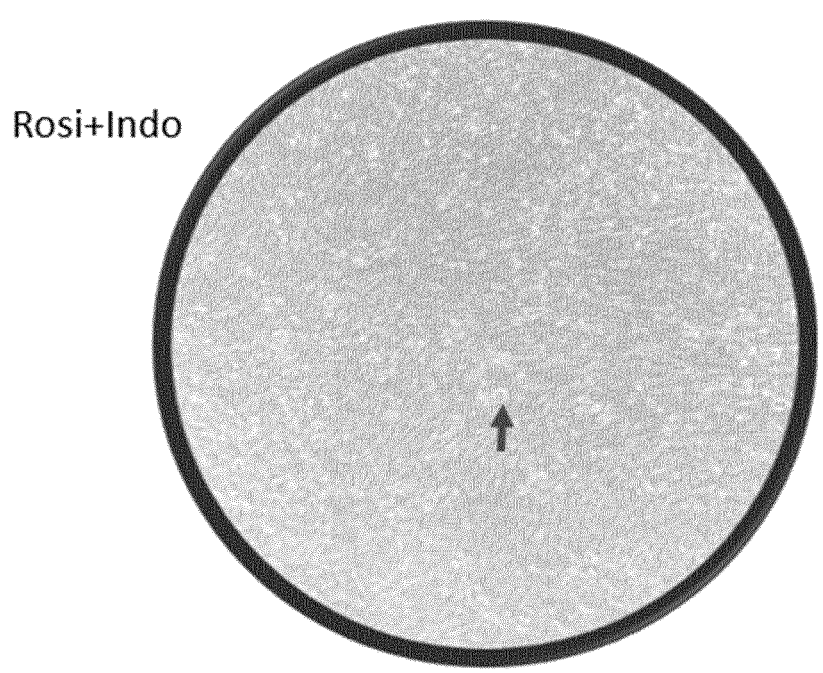
Figure 4:
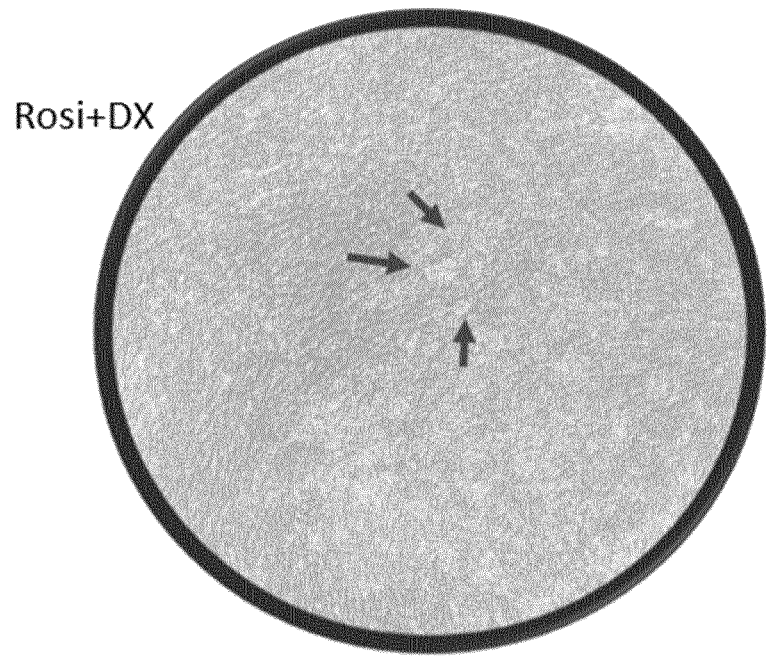
Figure 4:
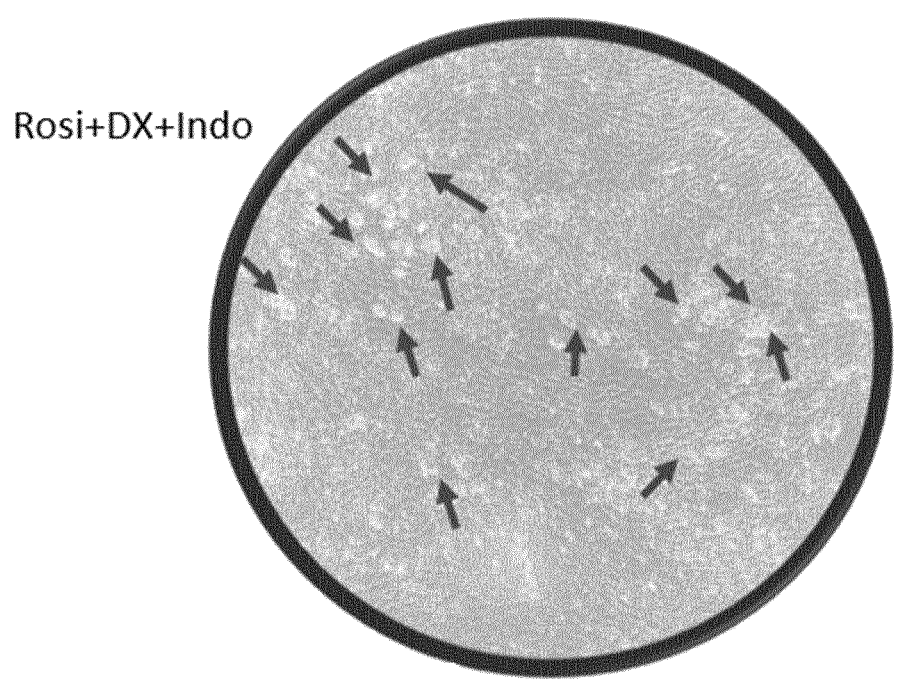

Example 2.2. Effect of the Thiazolidinediones on Adipocyte Differentiation and their Synergistic Effect with Corticoids and NSAID The pro-adipogenic profile of PPARG agonists like the thiazolidinediones was evaluated in the present invention, particularly their effect at an early stage (7 days) of the adipocyte differentiation process of pre-adipocytic cells. As shown in FIG. 2, rosiglitazone stimulation promoted the expression of the early differentiation marker gene ADIPOQ without augmenting the expression of the early, medium and late differentiation marker genes: FABP4, PPARG and PLIN2, respectively. Interestingly, the effect of rosiglitazone on the expression of all the differentiation marker genes studied was synergistically enhanced by the co-stimulation with corticoids (dexamethasone) and NSAID (indomethacin) (FIG. 2). This synergism was also observed in the early formation of lipid droplets in the cells, which meant a significant promotion of the adipogenic differentiation by these compounds (FIG. 4). Something similar occurs with pioglitazone. FIG. 3 displays the augment in FABP4 and ADIPOQ adipocytic marker genes expression exerted by pioglitazone. Nevertheless, this increase is significantly lower than the drug combination's one.

Example 2.3. The Thiazolidinediones Inhibit the WNT Signalling Pathway

Figure 5:
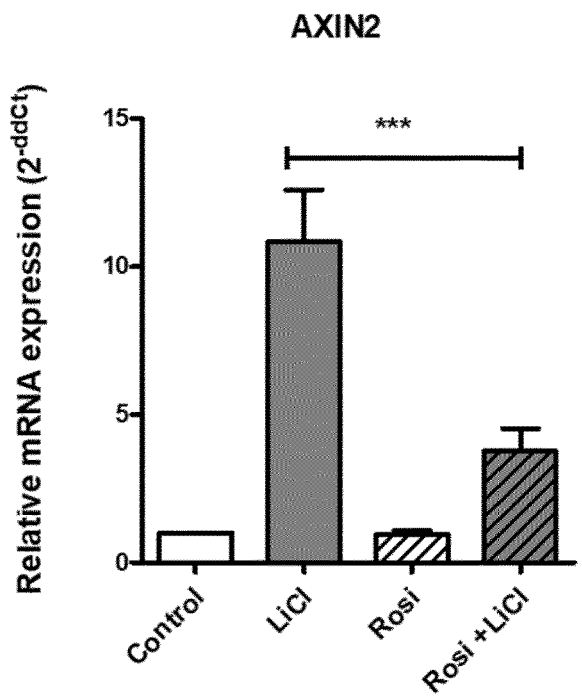
FIG. 5. WNT pathway inhibition by rosiglitazone. This figure shows how rosglitazone was able to significantly inhibit the activation of WNT pathway induced by two independent activators: A) LiCl and B) 6-bromoindirubin-3-oxim (BIO) on ATDC5 cells, which are precursor cells of a soft tissue. WNT activation and inhibition are represented by the rapid induction and inhibition of AXIN2 mRNA expression. *$p<0.05$; ***$p<0.001$ FIG. 6. WNT pathway inhibition by pioglitazone. This figure shows how pioglitazone was able to significantly inhibit the activation of WNT pathway induced by two independent activators: A) LiCl and B) 6-bromoindirubin-3-oxim (BIO) on ATDC5 cells, which are precursor cells of a soft tissue. WNT activation and inhibition are represented by the rapid induction and inhibition of AXIN2 mRNA expression. *$p<0.05$ FIG. 7. The combination of rosiglitazone, dexamethasone and indomethacin enhances osteoblast differentiation inhibition. This figure shows the effect of the thiazolidinediones (rosiglitazone) on osteoblast differentiation and its increased inhibitory effect with corticoids and NSAID. A precursor cell line was differentiated for 14 days to perform this experiment. It is observed that the highest inhibition of the expression of key osteoblastic marker genes: A) SPP1, B) GPNMB and C) BMP2 was only achieved by the combination of the three drugs *$p<0.05$; $p<0.01$; *$p<0.001$
Figure 5:
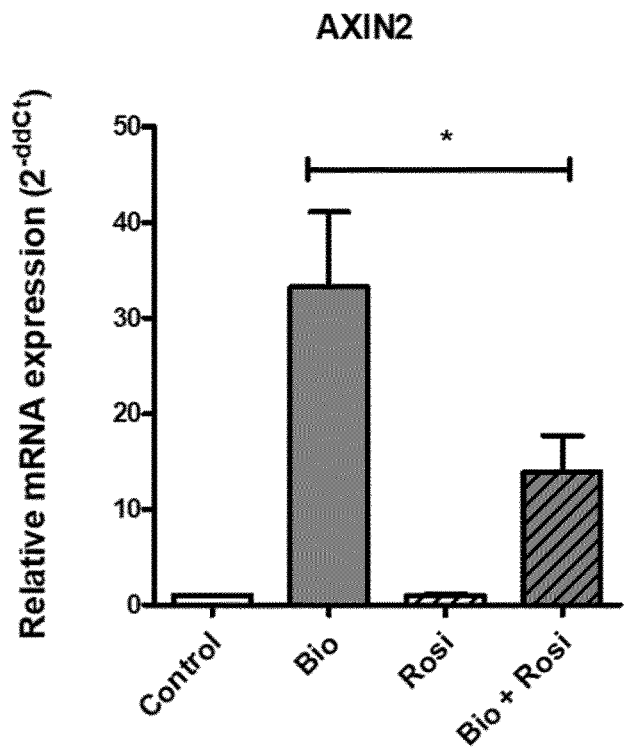
Figure 6:
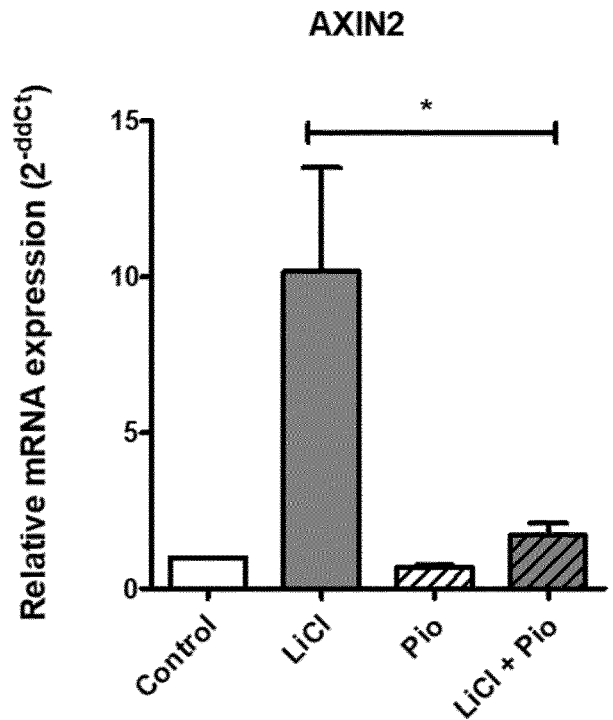
Figure 6:
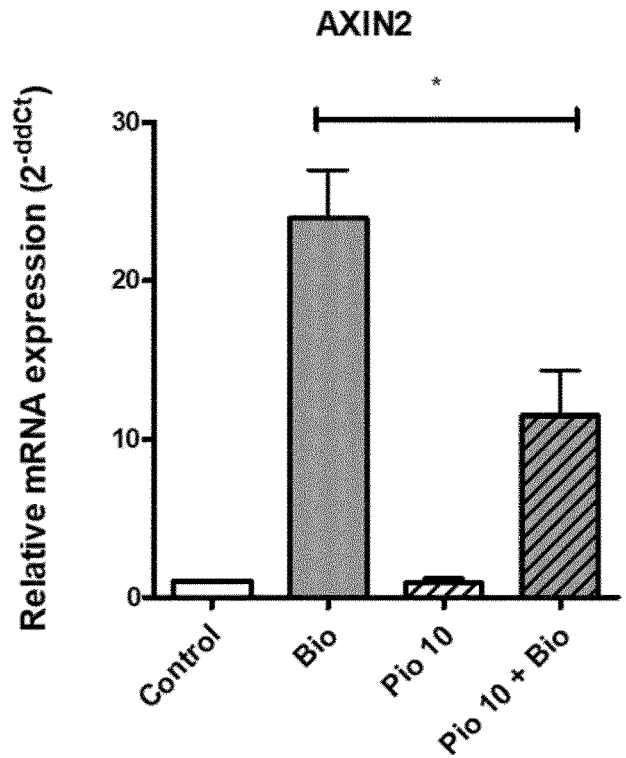

Prompted by the fact that the adipogenic environment was able to inhibit HObs growth and by the early pro-adipogenic effect of rosiglitazone and pioglitazone, it was decided to investigate the effect of thiazolidinediones on the activation of the WNT pathway. This pathway is one of the major anabolic signalling pathways in osteoblasts, that also plays a key role in the endochondral ossification. To do this, the activation of the WNT pathway was evaluated measuring the induction of AXIN2 gene expression in a pre-chondrogenic cell line. As described in FIG. 5, rosiglitazone was able to significantly inhibit the activation of WNT pathway induced by two independent activators (LiCl and 6-bromoindirubin-3-oxim (BIO)). As shown in FIG. 6, the thiazolidinedione pioglitazone exhibited the same behavior.

Figure 7:
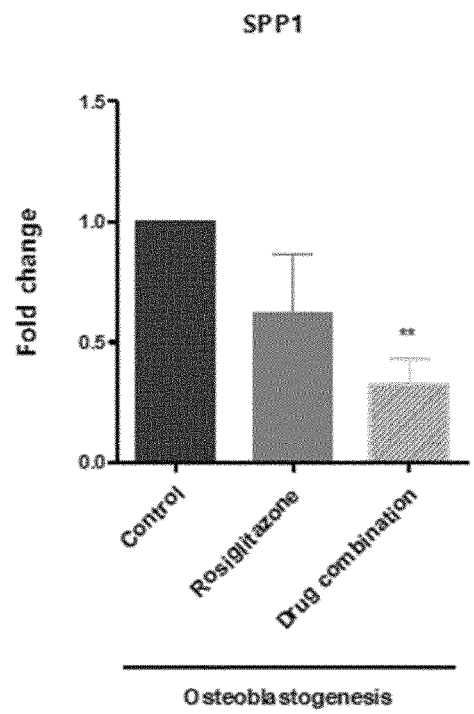
Figure 7:
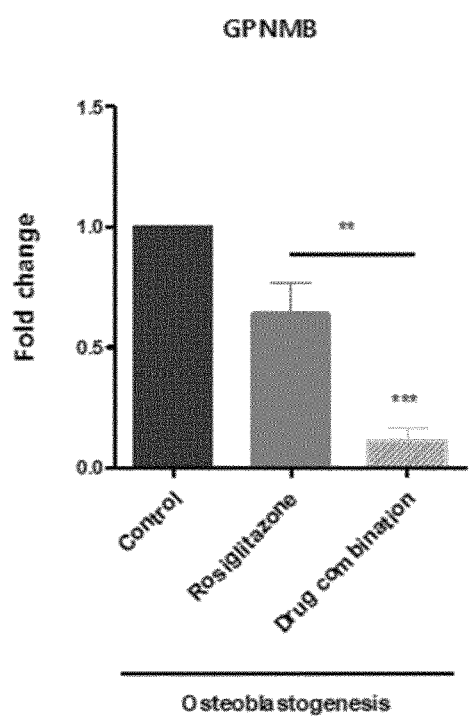
Figure 7:
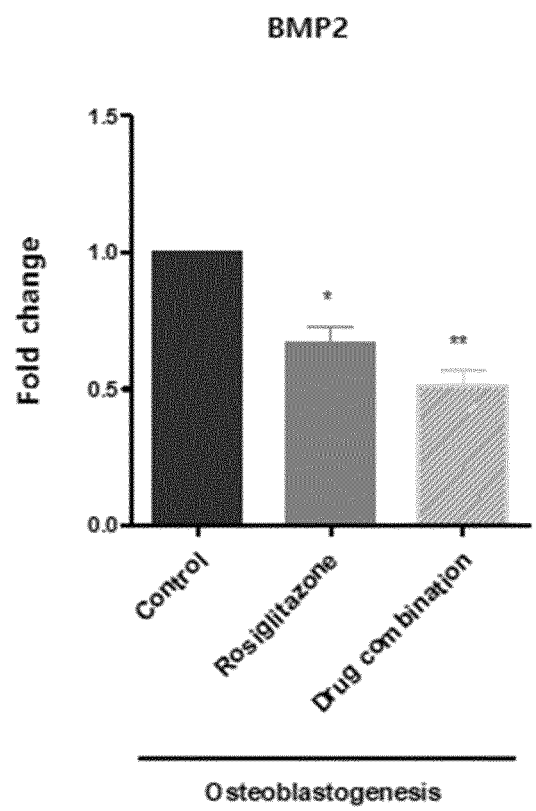

Example 2.4. Effect of the Thiazolidinediones on Osteoblast Differentiation and Their Enhanced Inhibitory Effect with Corticoids and NSAID Considering the strong inhibition of WNT signalling by the thiazolidinediones it was decided to further evaluate the potential inhibitory effect of these drugs on the osteoblast differentiation process. As shown in FIG. 7, rosiglitazone was able to reduce the expression of diverse differentiation markers (GPNMB and BMP2), which in turns meant that the thiazolidinediones inhibited osteoblast differentiation. Interestingly, as observed for the adipogenesis, the activity of rosiglitazone was enhanced by the co-stimulation with corticoids (dexamethasone) and NSAID (indomethacin) (FIG. 7), obtaining a significant decrease in the expression of above-mentioned differentiation markers, and in the early marker SPP1 too.

Example 2.5. Oral Administration of the Composition of the Invention

Nowadays, the three drugs that comprise the composition of the invention give rise to a new therapy which can be administered orally. However, oral presentation of pioglitazone does not allow certain dose adjustments for paediatric patients or patients with certain range of weight (they are only available 15 mg, and 30 mg tablets). Therefore, a new oral presentation would improve the treatment of these patients. In addition to this, a new oral formulation combining the three drugs would also be of interest since it will enhance patient's adherence to the treatment.

According to the pharmacokinetics parameters of each of the 3 drugs, optimum therapeutic doses were established in the present invention. However, it was observed that the therapeutic range of these compounds is very wide, specifically when the three drugs are administered together.

Optimum concentration available for the cells to achieve a maximal effect is as follows:

Pioglitazone (Pio): 10 μM.
Dexamethasone (Dx): 1 μM.
Indomethacin (Indo): 60 μM.

Calculation of the oral dose of pioglitazone:
  Maximum plasma dose 2 h after its oral administration.
  Linear increase of plasma concentration tested from 2 mg to 60 mg.
  Bioavailability: >80% (83 aprox.).
  Volume of distribution: 0.25 L/Kg.
  Binding to plasmatic proteins: >99%.
  According to these data the corresponding oral dose for pioglitazone could be 1 mg/kg/day. This dose is compatible with the safety of the drug since clinical trials showed that doses up to 180 mg/day are safe.

Calculation of the oral dose of dexamethasone:
  Bioavailability: 90%.
  Volume of distribution: 2 L/Kg (calculated from a specific dexamethasone formulation).
  Binding to plasmatic proteins: 70%-77%.
  According to these data the corresponding oral dose for dexamethasone could be 0.8721 mg/kg/day. Although this dose is an elevated dose, it is used in the clinic. However, there are data supporting the use of 0.08721 mg/kg/day dose to prevent the osteoblastogenesis.

Calculation of the oral dose of indomethacin:
  Bioavailability: total.
  Volume of distribution: not available.
  Binding to plasmatic proteins: >99%.
  Although a calculated dose for the 60 uM concentration could be determined, clinical data established that a 75 mg retard administration of indomethacin is enough to significantly reduce abnormal bone growth.

Example 2.6. Intravenous Administration of the Composition of the Invention

The intravenous administration of this therapy will be of interest for the prevention of abnormal bone growth when patients are in coma or the oral administration was not adequate. The plasmatic concentration of each drug should be the equivalent to the oral doses described above:
  Pioglitazone: 0.881 mg/Kg/day for its intravenous administration.
  Dexamethasone: 0.07 mg/Kg/day for its intravenous administration.
  Indomethacin: 75 mg/day for its intravenous administration in a retard delivery pattern or its equivalent in several non-retard doses.

Currently there are dexamethasone and indomethacin injectable formulations. However, there is not pioglitazone injectable formulation. As a result, to treat coma patients we propose the development of an intravenous injectable formulation for pioglitazone alone or together with dexamethasone and indomethacin. Considering that pioglitazone is a highly insoluble drug, its injectable formulation could improve its solubility by means of an adequate solvent or carrier such as cyclodextrins or even by using nanoparticles or liposomes. In order to determine the concentration of the drugs in the intravenous formulation it should be taken into account the data provided above about the binding to plasmatic proteins of each of the drugs and also the already described data about their half-life and clearance.

Example 2.7. Local Administration of the Composition of the Invention

The advantage of the local administration of this therapy is the fact that its effect would be maximal in the region of interest and minimal at systemic level, which means a very significant reduction on its side effects. For instance, local administration of this therapy would be an appealing option for abnormal bone growth in the surrounding tissues of a hip replacement surgery or abnormal bone growth recurrence after an excision surgery of an ectopic bone.

The local administration of this therapy will require, at least, the development of a pioglitazone injectable formulation. To develop this formulation, we will take the same considerations that for the intravenous formulation. In fact, the intravenous formulation would also work as a local administration formulation.

The requirements for the local formulation, despite the wide therapeutic range of this therapy, are that the formulation should provide in the area the optimum concentration to achieve the maximal effect:
  Pioglitazone (Pio): 10 uM.
  Dexamethasone (Dx): 1 uM.
  Indomethacin (Indo): 60 uM.

Example 2.8. Dosage Regimens

Depending in the situation and patient characteristics, the acute or chronic prevention of abnormal bone growth could involve different dosage regimens For the acute systemic prevention of abnormal bone growth or its recurrence after a surgery or a traumatic injury:

The therapy could start 3 days before the surgery or immediately after the traumatic injury and spans for 21 days more. However, with 14 days or less we could also expect a significant reduction in the development of abnormal bone growth. In certain patients, more than 21 days of treatment would also be related with an improvement on the abnormal bone growth incidence.

The initial daily doses for each drug would be:
  Pioglitazone: 1 mg/Kg oral dose and 0.881 mg/Kg for its intravenous administration.
  Dexamethasone: 0.08 mg/kg oral dose and 0.07 mg/Kg for its intravenous administration.
  Indomethacin: 75 mg (oral retard administration) or its equivalent in intravenous administration.

Considering the strong and wide therapeutic range of dexamethasone, to avoid a relevant immune suppression that might be undesirable in the context of an open wound or surgery, the dose of dexamethasone could be maintained for 2 weeks and slowly reduced afterwards. The reduction should be done in a way that we can avoid the corticoid deprivation syndrome.

The initial oral dosage regimen for paediatric patients could be:
  Pioglitazone: daily 1 mg/Kg for 2 weeks, starting 3 days before surgery. Following these 2 weeks, the dose will be maintained up to total 45 mg/day for 11 days more.
  Dexamethasone: daily 0.08 mg/Kg up to total 3 mg/day, for 2 weeks, starting 3 days before surgery. Following these 2 weeks, the dose will be reduced a 25% each 5 days until the total reduction of the dose.
  NSAID (indomethacin): 75 mg retard. Frequency: daily for 3 days before surgery and 21 after.

For the intravenous administration the concentrations will be adapted as described above.

For the acute local prevention of abnormal bone growth or its recurrence after a surgery or a traumatic injury:

As described above for the local injectable formulation, the objective of this via of administration is to obtain the following local optimum concentrations for the cells:
  Pioglitazone (Pio): 10 uM.
  Dexamethasone (Dx): 1 uM.
  Indomethacin (Indo): 60 uM.

The local administration of these compounds should not overcome systemically the doses described for the oral therapy. The therapy will last at least the same of the systemic treatment but considering the reduced side effects of this administration via, the therapy could be prolonged more time if it was necessary.

For the local prevention of the heterotopic ossification linked to genetic mutations, the doses and formulation of the therapy would be the same than for other types of heterotopic ossification. However, considering that these patients have an excessive osteoblastic metabolism the dose regimen and dose concentration of the therapy could be increased. For the chronic prevention of abnormal bone growth which is mainly associated to genetic mutations:

The therapy presented here when administered systemically could also work for this chronic form of heterotopic ossification. However, several considerations should be taken into account. The use of corticoids in a chronic fashion is associated with strong side effects. Therefore, the risk/benefit of the full therapy should be evaluated carefully. However, although the maximal effect of this therapy is associated with the presence of the three drugs, pioglitazone alone or in combination with NSAID can significantly reduce osteoblast metabolism and therefore the ectopic bone growth. In this scenario corticoids could be administered in a reduced dose or in a periodic fashion in order to avoid major side effects. Alternatively, corticoids could be used locally to promote the effect of the therapy in a specific region of interest.

The invention claimed is:

1. A method for preventing or treating abnormal bone growth in a subject, the method comprising administering to the subject a therapeutically effective amount of a combination drug product comprising:
   a thiazolidinedione selected from the group consisting of rosiglitazone, pioglitazone, or a combination thereof;
   a corticoid comprising dexamethasone; and
   an anti-inflammatory drug comprising indomethacin.

2. The method according to claim 1, wherein the thiazolidinedione is rosiglitazone or pioglitazone.

3. The method according to claim 1, wherein the corticoid is dexamethasone.

4. The method according to claim 1, wherein the anti-inflammatory drug is indomethacin.

5. The method according to claim 1, wherein the thiazolidinedione, the corticoid and the anti-inflammatory drug are administered together.

6. The method according to claim 1, wherein the thiazolidinedione, the corticoid and the anti-inflammatory drug are not administered together.

7. The method according to claim 1, wherein the thiazolidinedione, the corticoid and the anti-inflammatory drug are administered by a route independently selected from the group consisting of an oral administration, an intravenous administration and a local administration.

8. The method according to claim 1, wherein the abnormal bone growth is selected from the group consisting of a heterotopic ossification, an osteophyte, a syndesmophyte, and any combination thereof.

9. The method according to claim 1, wherein the abnormal bone growth is acute or chronic heterotopic ossification.

10. The method according to claim 1, wherein the abnormal bone growth includes a heterotopic ossification in at least one soft tissue.

* * * * *